United States Patent
Farrugia et al.

(10) Patent No.: US 9,888,858 B2
(45) Date of Patent: Feb. 13, 2018

(54) METHOD AND APPARATUS FOR DETECTING CARDIAC SIGNALS

(75) Inventors: Steven Paul Farrugia, Lugarno (AU); Darius George Chapman, Blackwood (AU)

(73) Assignee: ResMed Limited (AU)

( * ) Notice: Subject to any disclaimer, the term of this patent is extended or adjusted under 35 U.S.C. 154(b) by 1235 days.

(21) Appl. No.: 13/988,809

(22) PCT Filed: Nov. 14, 2011

(86) PCT No.: PCT/AU2011/001470
§ 371 (c)(1),
(2), (4) Date: May 22, 2013

(87) PCT Pub. No.: WO2012/068613
PCT Pub. Date: May 31, 2012

(65) Prior Publication Data
US 2013/0237793 A1    Sep. 12, 2013

Related U.S. Application Data

(60) Provisional application No. 61/416,445, filed on Nov. 23, 2010.

(51) Int. Cl.
*A61B 5/0402* (2006.01)
*A61B 5/0408* (2006.01)
(Continued)

(52) U.S. Cl.
CPC ........ *A61B 5/0245* (2013.01); *A61B 5/02405* (2013.01); *A61B 5/02438* (2013.01);
(Continued)

(58) Field of Classification Search
CPC . A61B 5/024; A61B 5/02405; A61B 5/02438; A61B 5/0402; A61B 5/0408;
(Continued)

(56) References Cited

U.S. PATENT DOCUMENTS 4,875,477 A * 10/1989 Waschke ............ A61B 5/02438
128/206.21
5,353,793 A * 10/1994 Bornn .................. A61B 5/0006
600/386
(Continued)

FOREIGN PATENT DOCUMENTS

CN            1409646 A     4/2003
CN          101400296 A     4/2009
(Continued)

OTHER PUBLICATIONS

Supplementary European Search Report for Application No. EP11843003 dated Aug. 3, 2015.
(Continued)

Primary Examiner — Lee S Cohen
Assistant Examiner — Erin M Cardinal
(74) Attorney, Agent, or Firm — Lerner, David, Littenberg, Krumholz & Mentlik, LLP

(57) ABSTRACT

Devices and systems provide methods for detecting cardiac signals from head or facial biopotential sensors. In one embodiment, a facial biopotential signal is measured by a set of sensors. A processor derives a cardiac signal from the facial biopotential signal. Optionally, heart rate is detected from the cardiac signal. Heart rate variability may be determined and evaluated by the processor to generate warnings or messages from the evaluation. One or more head or facial biopotential electrodes for measuring the facial biopotential signal may be integrated in or at a contact surface of head support structures such as a headgear support or respiratory treatment mask. In some such embodiments a controller of a respiratory treatment apparatus may serve as a cardiac signal detector by processing the facial biopotential signal from the sensors and may make control adjustments or generate warnings based on an evaluation of detected signals.

77 Claims, 9 Drawing Sheets

(51) Int. Cl.

| | |
|---|---|
| *A61B 5/0245* | (2006.01) |
| *A61B 5/024* | (2006.01) |
| *A61B 5/0476* | (2006.01) |
| *A61M 16/00* | (2006.01) |
| *A61M 16/06* | (2006.01) |
| *A61M 16/08* | (2006.01) |
| *A61B 5/00* | (2006.01) |

(52) U.S. Cl.
CPC .......... *A61B 5/0402* (2013.01); *A61B 5/0408* (2013.01); *A61B 5/0476* (2013.01); *A61B 5/4836* (2013.01); *A61B 5/6803* (2013.01); *A61B 5/6814* (2013.01); *A61B 5/7278* (2013.01); *A61M 16/0051* (2013.01); *A61M 16/0066* (2013.01); *A61M 16/0069* (2014.02); *A61M 16/0633* (2014.02); *A61M 16/0683* (2013.01); *A61M 16/0875* (2013.01); *A61B 5/4818* (2013.01); *A61M 2016/0027* (2013.01); *A61M 2016/0036* (2013.01); *A61M 2205/13* (2013.01); *A61M 2205/3569* (2013.01); *A61M 2205/3592* (2013.01); *A61M 2205/502* (2013.01); *A61M 2230/04* (2013.01)

(58) Field of Classification Search
CPC ... A61B 5/4806; A61B 5/4818; A61B 5/6803; A61B 5/6814; A61B 5/6819; A61B 5/682; A61B 5/6822; A61B 2560/0468; A61B 2562/0214
USPC .............................. 600/383, 509; 128/204.21
See application file for complete search history.

(56) References Cited

U.S. PATENT DOCUMENTS

| | | | |
|---|---|---|---|
| 6,032,065 A | 2/2000 | Brown | |
| 7,204,250 B1 | 4/2007 | Burton | |
| 7,942,824 B1* | 5/2011 | Kayyali | ................. A61B 5/021 |
| | | | 128/204.23 |
| 2003/0158497 A1* | 8/2003 | Graham | ............... A61B 5/0496 |
| | | | 600/558 |
| 2004/0163648 A1* | 8/2004 | Burton | ............... A61B 5/04085 |
| | | | 128/204.21 |
| 2005/0076905 A1* | 4/2005 | Stahmann | ............ A61B 5/0031 |
| | | | 128/203.14 |
| 2005/0131288 A1* | 6/2005 | Turner | ................. A61B 5/0006 |
| | | | 600/391 |
| 2006/0100538 A1* | 5/2006 | Genger | ................. A61M 16/00 |
| | | | 600/544 |
| 2006/0122478 A1* | 6/2006 | Sliepen | .............. A41D 13/1281 |
| | | | 600/383 |
| 2007/0142738 A1 | 6/2007 | Hung | |
| 2007/0208269 A1* | 9/2007 | Mumford | ............ A61B 5/0002 |
| | | | 600/546 |
| 2008/0091090 A1* | 4/2008 | Guillory | ............... A61B 5/0478 |
| | | | 600/301 |
| 2008/0127978 A1 | 6/2008 | Rubin et al. | |
| 2010/0179389 A1* | 7/2010 | Moroney, III | ...... G06F 19/3406 |
| | | | 600/301 |
| 2010/0240982 A1* | 9/2010 | Westbrook | ............ A61B 5/087 |
| | | | 600/391 |
| 2011/0275921 A1* | 11/2011 | Revishvili | .......... A61B 5/04023 |
| | | | 600/382 |

FOREIGN PATENT DOCUMENTS

| | | |
|---|---|---|
| JP | 63294834 | 1/1988 |
| JP | 2003516825 A | 5/2003 |
| WO | 0143804 A1 | 6/2001 |
| WO | 01043804 A1 | 6/2001 |
| WO | 2005118042 A2 | 12/2005 |
| WO | 2007100959 A2 | 9/2007 |
| WO | 2009033181 A2 | 9/2007 |

OTHER PUBLICATIONS

Chinese Office Action for Application No. 201180056472.3 dated Jul. 3, 2014.
International Search Report and Written Opinion, PCT/AU2011/001470, dated Mar. 8, 2012.

* cited by examiner

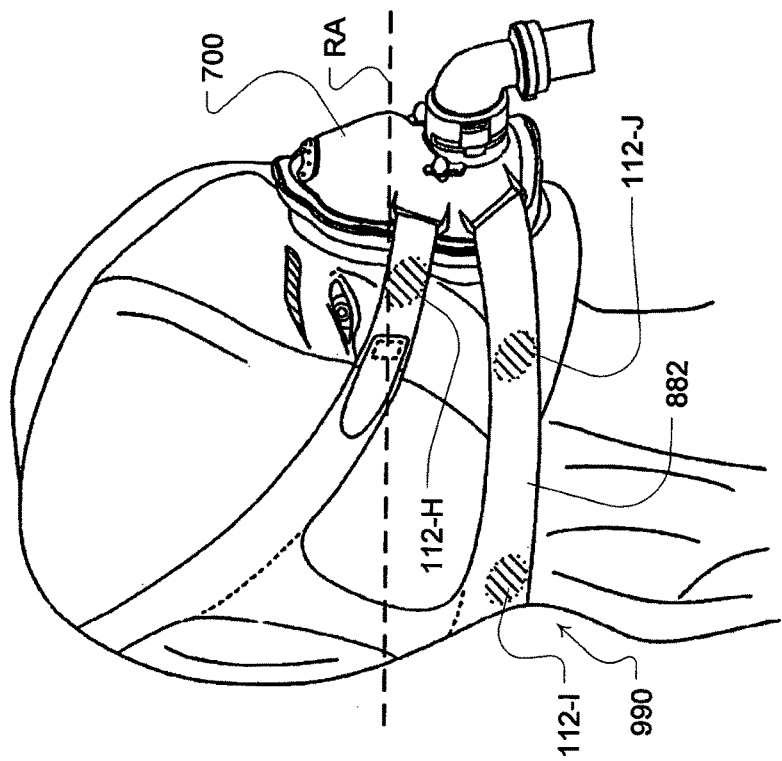
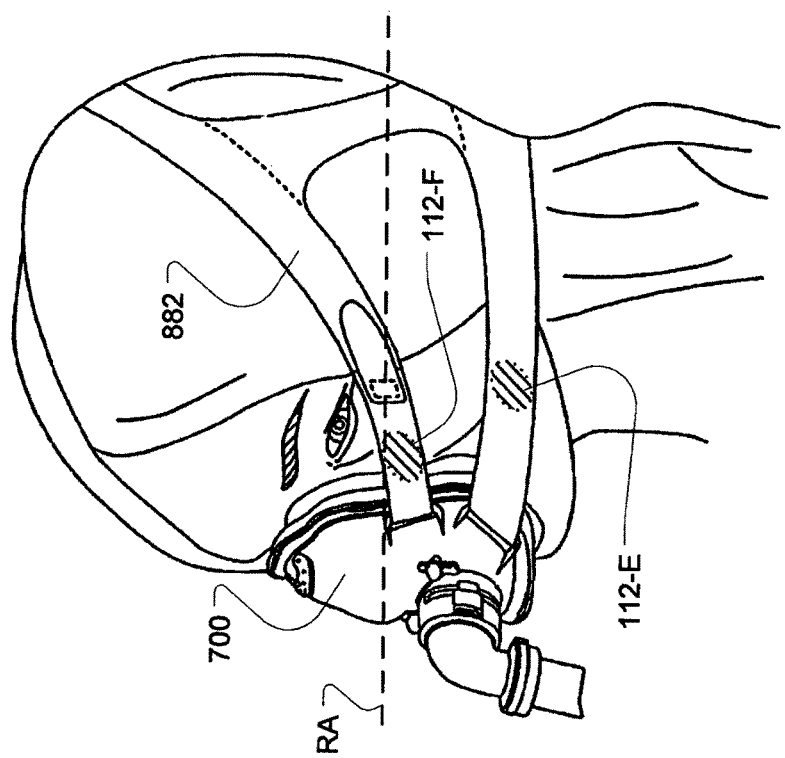

METHOD AND APPARATUS FOR DETECTING CARDIAC SIGNALS

CROSS REFERENCE TO RELATED APPLICATIONS

The present application is a national phase entry under 35 U.S.C. § 371 of International Application No. PCT/AU11/01470, filed Nov. 14, 2011, published in English, which claims priority from U.S. Provisional Patent Application No. 61/416,445, filed on Nov. 23, 2010, all of which are incorporated herein by reference.

FIELD OF THE TECHNOLOGY

The present technology relates to methods and apparatus for detecting cardiac signals. More particularly, some embodiments of the technology relate to detecting cardiac signals from the biopotential of the head or face.

BACKGROUND OF THE TECHNOLOGY

Cardiac signals are often detected by ah electrocardiogram. Electrocardiography (ECG or EKG) is a transthoracic interpretation of the electrical activity of the heart over time performed by detecting the electrical activity from skin electrodes.

The ECG detects the activity by amplifying the small electrical changes at the skin of the chest that are caused when the heart muscle depolarizes during each heart beat. Changes in voltage attributable to the electrical changes are detected by two electrodes placed on either side of the heart.

It will be appreciated that there is a need in the art for improved techniques and devices for detecting cardiac signals.

SUMMARY OF THE TECHNOLOGY

Aspects of some embodiments of the present technology may involve a detection of cardiac signals.

Further aspects of some embodiments of the present technology may involve the detection of cardiac signals from biopotential sensors such as head or facial contact electrodes, head or facial non-contact electrodes, etc.

Still further aspects of some embodiments of the present technology may involve a detection of cardiac signals by respiratory treatment apparatus, such as a ventilator or positive airway pressure treatment apparatus.

Additional aspects of some embodiments of the present technology may involve the detection of cardiac signals from biopotential sensors integrated in headgear for the sensors or in the components of a respiratory mask, such as a mask frame or mask cushion, and/or the head gear support for a respiratory mask such as a mask strap.

Some embodiments of the technology may involve a method for detecting a cardiac signal. The method may include measuring a facial biopotential signal from a set of electrodes connected to a patient. This may involve detecting by a processor a cardiac signal from the facial biopotential signal.

Some embodiments of the present technology include a device for detecting a cardiac signal. The device may include a set of facial electrodes. The device may further include a processor, coupled with the set of facial electrodes. Such a processor may be configured to control a detection of a cardiac signal from a facial biopotential signal measured with the set of facial electrodes.

Some embodiments of the present technology may also include a respiratory treatment apparatus. The apparatus may include a patient interface including a set of facial electrodes. The apparatus may also include a flow generator adapted to be coupled to the patient interface. The flow generator may generate a flow a breathable gas to the patient interface. The apparatus may also include a processor, coupled with the flow generator and adapted to couple with the set of facial electrodes, the processor may be configured to control the flow generator, and to control a detection of a cardiac signal from a facial biopotential signal measured with the set of facial electrodes.

In some cases, the measuring may involve determining a voltage difference between signals of at least two electrodes of the set of electrodes. It may also involve determining field strength with the set of electrodes, the set of electrodes comprising a non-contact sensor. Still further, it may involve measuring current between two electrodes of the set of electrodes.

Optionally, the detecting may involve signal processing of the facial biopotential signal. For example, the processing may include filtering the facial biopotential signal.

Moreover, the embodiments may further include a determination of a heart rate from the cardiac signal. This may involve detecting peaks within the cardiac signal. It may further involve determining intervals between detected peaks. Optionally, the determined intervals may be filtered to remove determined intervals shorter than a threshold. In some embodiments, an average of the determined intervals may be calculated.

Optionally, the embodiments may further involve determining heart-rate variability based on repeatedly determining the heart rate.

In some cases, the set of electrodes may include a first electrode and a second electrode where the first electrode is a sub-rhinal facial electrode. Optionally, the first electrode may also be a sagittal-left facial electrode. Optionally, the second electrode may include a ground electrode.

In some embodiments, the first electrode may be formed as a portion of headgear. In some such cases, the first electrode may be formed of a conductive ink. Still further, the first electrode may be a fabric electrode formed of conductive thread. Optionally, the first electrode may be configured as a portion of a respiratory mask. The first electrode may even be embedded in a non-conductive polymer of a mask cushion and may be a skin contact electrode or a non-contact electrode.

In some cases, the first electrode may be configured as a portion of a headgear support for a respiratory mask. In some embodiments, the set of electrodes may be formed as a portion of a respiratory mask. Still further the set of electrodes may be configured as a portion of a headgear support for a respiratory mask.

Still further embodiments of the technology may include a patient interface device for a respiratory treatment apparatus. The patient interface device may include a set of electrodes that includes a first facial electrode. The set of electrodes may be adapted for coupling with a signal interface of a processor of a respiratory treatment apparatus for detection of a cardiac signal from a facial biopotential signal measured with the set of electrodes. Optionally, the patient interface device may be configured to conduct a flow of breathable gas from a flow generator of the respiratory treatment apparatus.

Optionally, the set of electrodes may include a second electrode, wherein the first electrode is a sub-rhinal electrode. Still further, the first electrode may be a sagittal-left electrode. The second electrode may be a ground electrode.

In some cases, the patient interface device may also include a respiratory mask. In such a case, the first electrode may be positioned on a facial contact surface of the respiratory mask. In some embodiments, the patient interface device may include a headgear support for a respiratory mask. In such a case, the first electrode may be positioned on a facial contact surface of the headgear support. Optionally, the first electrode may be configured as a portion of headgear.

In some cases, the first electrode of the patient interface may be formed of a conductive ink or as a fabric electrode formed of conductive thread. Optionally, the first electrode of the patient interface may be embedded in a non-conductive polymer of a mask cushion and may be a skin contact electrode or a non-contact electrode.

Various aspects of the described example embodiments may be combined with aspects of certain other example embodiments to realize yet further embodiments.

Other features of the technology will be apparent from consideration of the information contained in the following specification.

BRIEF DESCRIPTION OF THE DRAWINGS

The present technology is illustrated by way of example, and not by way of limitation, in the figures of the accompanying drawings, in which like reference numerals refer to similar elements including:

FIG. 8 is a left side view of another respiratory treatment mask with biopotential sensors integrated in a headgear support for the mask;

FIG. 9 is a right side view of the respiratory treatment mask of FIG. 8 with additional biopotential sensors integrated in the headgear support for the mask;

DETAILED DESCRIPTION

Figure 1:
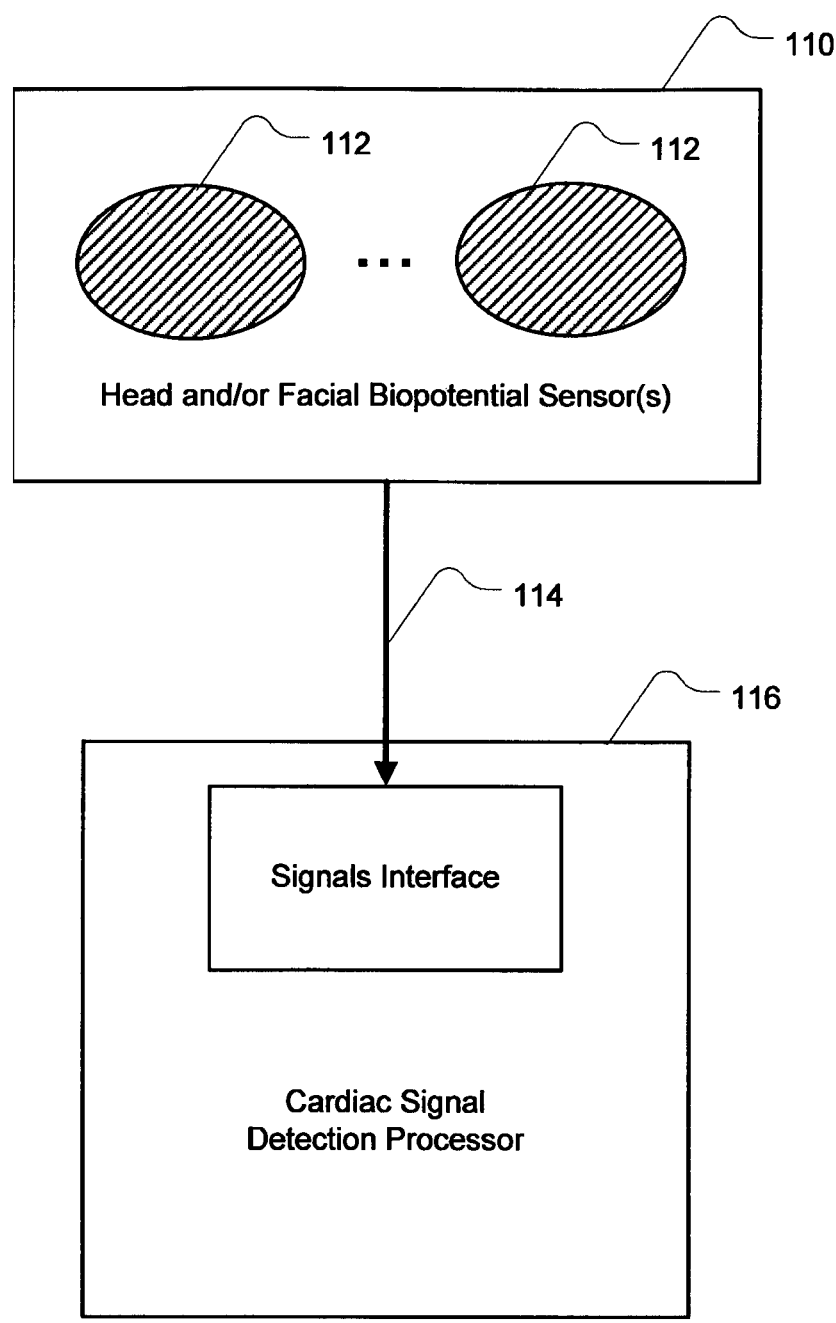
FIG. 1 illustrates example components of a monitoring device to implement cardiac signal detection based on head and/or facial biopotential sensors.

The present technology involves methods and devices for the detection of cardiac signals. Such embodiments of the technology may derive cardiac signals from biopotential sensors. As illustrated in FIG. 1, a typical embodiment of the technology employs a set of biopotential sensors 110. The set of biopotential sensors typically includes one or more head and/or facial biopotential sensors such as electrodes 112. Such sensors can be configured for detection of electrical signals at or near the contact surface of the skin of the face or head of a patient. The head or facial biopotential signal(s) 114 produced by these sensors may then be processed by a cardiac signal detection processor 116 to detect or derive a cardiac signal from the head or facial biopotential signal.

With such cardiac signal detection, a processor of an apparatus may then optionally analyze the signal or data representing the signal to determine heart rate variability or other metrics, such as heart related metrics, from the signal. The metrics may then be analyzed to assess autonomic status or imbalance, e.g. indicators of diabetes or other autonomic disorders. For example, the cardiac signal may be analyzed by a processor of an apparatus to provide an alert or message to declining autonomic status or current imbalance. Similarly, the signals and metrics may also be analyzed by a processor to assess cardiovascular trends or status and provide similar alerts or messages. By way of further example, the signal may serve as a basis for detecting parameters for automated analysis of heart condition such as a heart failure condition indicator described in U.S. patent application Ser. No. 12/483,357 (filed Jun. 12, 2009), the entire disclosure of which is incorporated herein. Similarly, it may be analyzed to serve as part of an automated sleep stage detector, such as a detector that may classify REM or Awake stages of sleep based on analysis of the cardiac signal and additional data from sensors of a device.

In some such embodiments, automated patient analysis of metrics derived or detected from the biopotential signals or cardiac signals may optionally include combined metrics based on signals from additional sensors described herein. For example, a combined patient analysis metric may be derived from signal processing or analysis of some or all of pressure signals, flow signals and/or biopotential signals. In one such embodiment, these signals may be recorded on a common time scale to permit assessment of the signals at certain times. For example, a metric based on a detected cardiac signal or biometric signal may be assessed during certain times of a patient respiratory cycle. In such a case, for example, the cardiac signal may be particularly assessed during times of an inspiration phase or an expiration phase by detecting these respiratory phases from flow and/or pressure signals and analyzing the cardiac signal in association with one or more of the detected phases.

Thus, a processor may be configured to implement particular methodologies to detect or derive the cardiac signal from the head or facial biopotential signals and analysis thereof such as by the algorithms described in more detail herein. For example, a device controller or processor may include integrated chips, such as application specific integrated chip(s), a memory and/or other control instruction, data or information storage medium with the methodologies. Thus, programmed instructions encompassing the methodologies may be coded on integrated chips or in the memory of the device. Such instructions may be loaded as software or firmware using an appropriate data storage medium.

Figure 2:
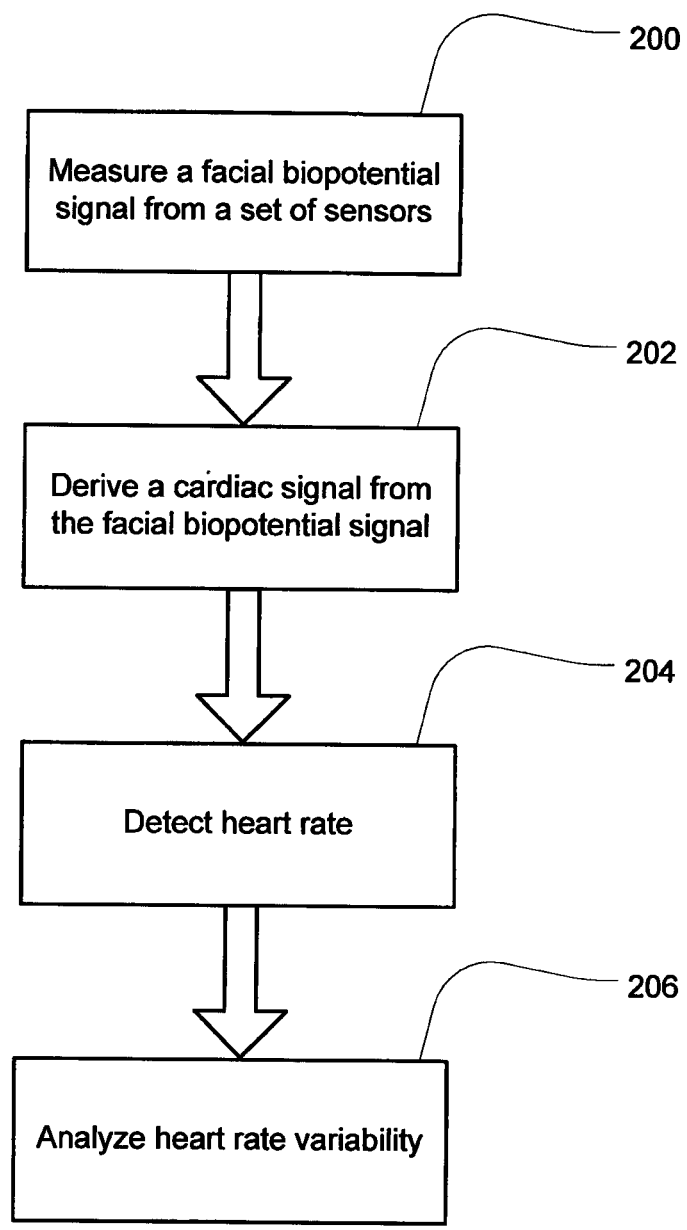
FIG. 2 is an example embodiment of a methodology for a controller or processor to detect cardiac signals of the current technology.

An example methodology for a processor of such an apparatus to detect a cardiac signal is illustrated in the flow chart of FIG. 2. At 200, one or more head or facial biopotential signals from a set of sensors or electrodes on or near a patient are measured. At 202, a cardiac signal is detected or derived from the head or facial biopotential signal(s). Optionally, at 204 a heart rate may be detected from the cardiac signal and at 206 a heart rate variability may be analyzed. For example, detected heart rates may be determined over time and stored in the memory of a processor. Changes to the heart rates may then be assessed. For example, if the changes meet a certain threshold such a comparison may then serve as a basis to trigger a message or warning concerning the change.

Figure 3:
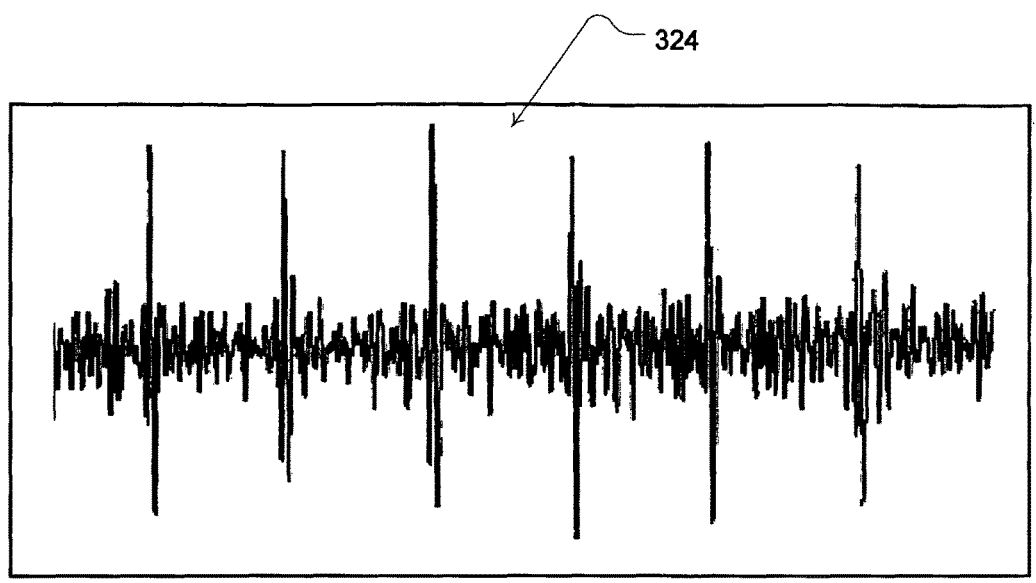
FIG. 3 illustrates a facial biopotential signal detectable with the example sensors of FIG. 1.

In one such embodiment, a heart rate may be determined from a cardiac signal by processing the head or facial biopotential signal. As illustrated in FIG. 3, cardiac signals appear as high amplitude, high frequency landmarks within the facial biopotential signal 324. Signal processing may be employed to separate or otherwise filter the "noise" of the head or facial biopotential signal and enhance the cardiac components. In one such case, a cardiac signal 424 such as the example of FIG. 4 may be derived.

For example, signal processing may be implemented to filter and/or smooth the biopotential signal. In some cases depending on the particular sensors and locations, frequency characteristics of the noise components attributable to the head or face (i.e., the signal components between the cardiac related QRS complexes, which are the deflections of the signal corresponding to the depolarization of the right and left ventricles) may indicate peak noise strength at low frequencies (e.g., about less than 8 Hz). Typically, the frequency of the QRS component may be between about 10-30 Hz. Thus, filters may be employed to band pass the biopotential signal such as in a band pass range of about 5-30 Hz. However, other filtering ranges or frequency cut-offs may be implemented and may depend on sensor location.

Smoothing may also be performed so as to enhance the high amplitude, relatively high frequency components of the signal and attenuate others. This may be accomplished by an adaptive low pass filter. Such a filter may adapt its response based on the input signal. For example, the filter may have feedback to refine the values of filter coefficients and its frequency response.

Figure 4:
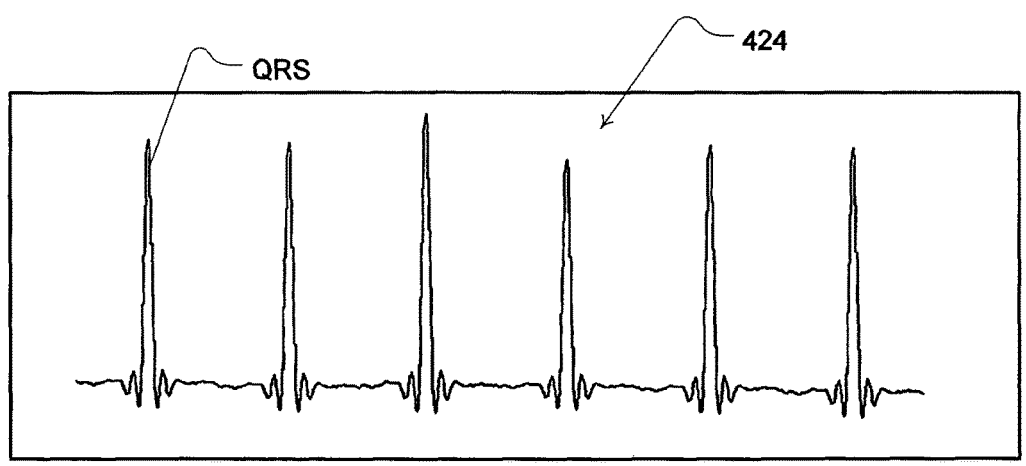
FIG. 4 illustrates an example cardiac signal derivable by processing of a head or facial biopotential signal, such as the signal of FIG. 3.

Such signal processing can be applied to the example facial biopotential signal of FIG. 3 to derive the example cardiac signal of FIG. 4. The processing of the smoothing and/or filtering may optionally be performed by any combination of hardware and/or software.

Heart rate may then be more easily detectable from the cardiac signal as a result of the processing of the head or facial biopotential signal. For example, in some embodiments, heart rate may be determined by detecting the cardiac related peaks, in which a thresholding algorithm may be employed. Such a processing methodology may work in several steps by detecting peaks above a threshold and determining intervals between peaks. Optionally, non-physiological peaks may be removed or disregarded. For example, each QRS peak of the signal may be detected by detecting peaks (e.g., a local maximum) and only considering peaks above a threshold (e.g., discarding peaks at or below a threshold). Optionally, peaks above a further threshold may be disregarded (e.g., peaks related to some signal artifact other than a cardiac peak.) Optionally, such peak threshold(s) may be pre-set value(s) or may be manually selected by a user interface of a monitor. Alternatively, thresholds may be determined more dynamically by processing of the signal. Thus, the threshold may be set as a function of the biopotential signal such as the noise of the signal. For example, when the amplitude of the cardiac peaks (QRS components) are, generally higher than the noise components of the signal and the noise components are more frequent as shown in FIG. 3, a threshold may be automatically chosen based on a determined average of the all of the amplitudes of the noise peaks and cardiac peaks in some desired time length of the signal. Thus, the threshold may be automatically set at, or some margin value above, the average of all of the detected peaks of the chosen time length. For example, the margin value may be set as some portion of a difference between a max peak and the average peak. Peaks above that threshold then may be considered QRS components or cardiac peaks and/or peaks at or below that threshold may be disregarded. Other methods may also be implemented in automatically detecting the cardiac peaks.

With the detected cardiac peaks, intervals may then be determined between them. For example, this may be done by determining the time difference between each consecutive peak or a number of samples in the signal between the sample numbers associated with the consecutive peaks. Optionally, further filtering may be performed to remove non-physiological peaks according to the interval length. For example, peaks associated with intervals shorter than an interval threshold may be disregarded. For example, where the interval time of a current peak from the prior peak is less than about 200 ms the current peak may be disregarded.

Based on the remaining intervals, a heart rate may then be calculated. For example, an average interval time may be determined. In such an embodiment, the interval average may be calculated with the intervals from a desired time length of the cardiac signal such as a time length on the order of minutes (e.g., 1 minute, two minutes etc.) This may be then used to determine, the heart rate (e.g., 1/average_interval_time). Still further a count of the number of intervals or peaks during the time length of the cardiac signal (e.g., one minute) may serve as the heart rate. Other methods for determining heart rate from the signal may also be employed. Such heart rate values may be periodically recorded over time for further analysis, such as for an assessment of heart rate variability as previously discussed.

Figure 5:
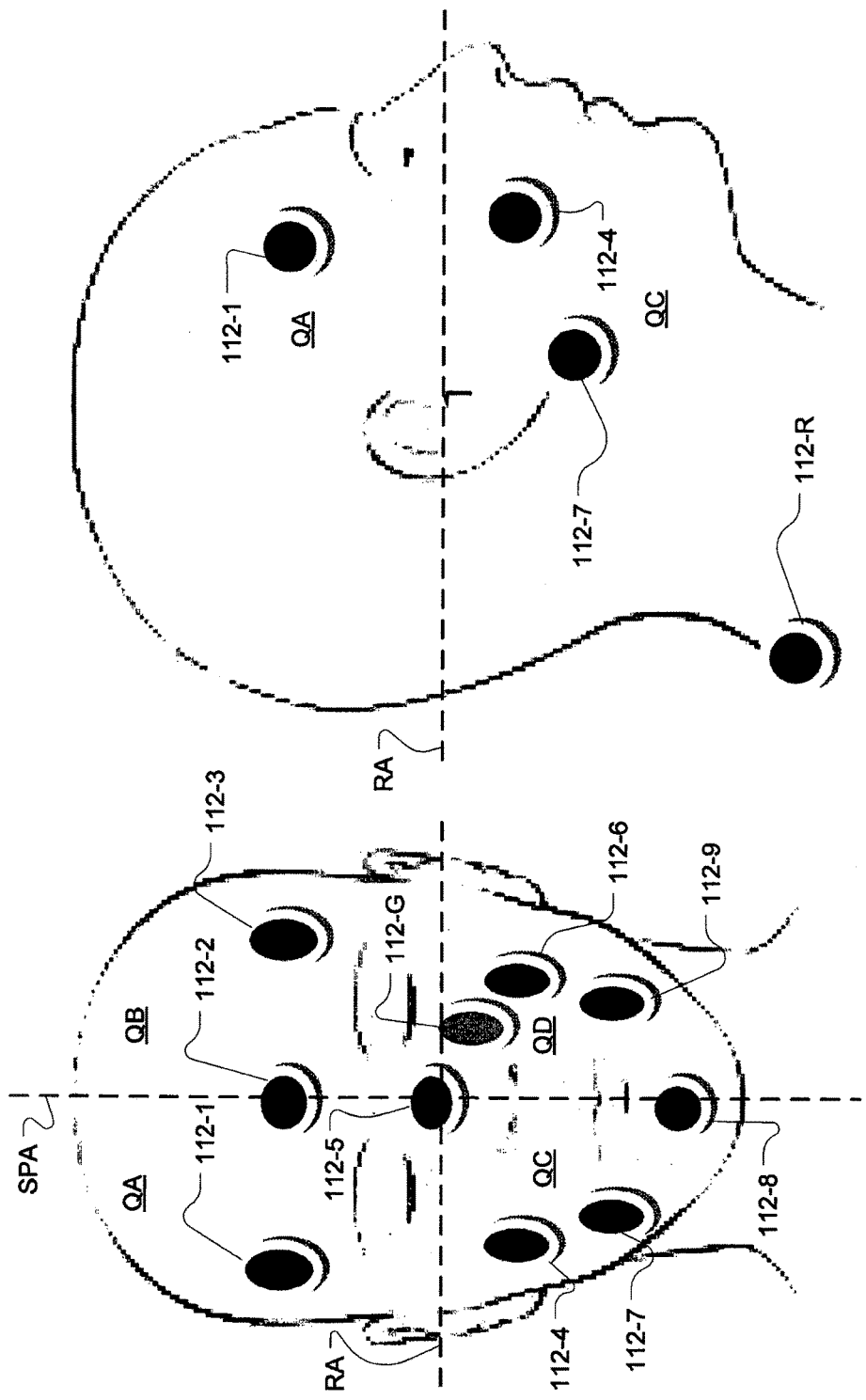
FIG. 5 illustrates example sensors and locations for head and/or facial based biopotential measurement in some embodiments of the present technology.

As previously discussed, the biopotential signal is measured with a set of one or more head or facial biopotential sensors. Examples of these head or facial biopotential sensors are illustrated in FIG. 5. Typically, two electrodes may be employed for determining a biopotential signal, which may be measured as a difference in the readings across the two electrodes. Optionally, the biopotential signal may be a measure of voltage, current or field strength using suitable sensors.

Thus, the biopotential sensors may be implemented as skin contact electrodes. For example, the electrode may be applied directly to the skin using a dry electrode or indirectly to the skin using an electrolyte gel or other conductive element or paste between the skin and electrode. Optionally, the biopotential sensors may be implemented as non-contact electrodes. For example, one or more electrodes may be embedded in a non-conductive component, such as a polymer (e.g., silicone), and may be located near the skin with the non-conductive component separating the skin and the electrode. Typically, such non-contact sensors may be utilized to measure the biopotential signal by detecting field strength.

Generally, the electrodes of the biopotential sensors may be formed with any suitable metal or conductor. For example, electrodes may be formed with conductive inks, such as in the case of printing or dying the electrode on other components. For example, conductive inks may be employed to print or dye an electrode on a headgear strap, a mask cushion, a mask frame or some other headgear. Similarly, the electrode may be formed as a fabric or cloth electrode. For example, an electrode may be formed or weaved with conductive threads or fine wire. For example, cloth may be impregnated with the wires or threads. Optionally, such an electrode may be weaved into the fabric of a strap of headgear or a headgear support. Optionally, electrodes may be constructed from or embedded in a conductive polymer.

Accordingly, in a typical embodiment, a first head or facial biopotential sensor or electrode may be employed as illustrated in FIG. 5. A second sensor or electrode may also be employed. However, the second sensor may, but does not need to be, located in a position on the head or face of the patient. For example, the second electrode may optionally be a neck electrode 112-R or other electrode. In a typical example embodiment, two or more of the electrodes 112-1, 112-2, 112-3, 112-4, 112-5, 112-6, 112-7, 112-8, 112-9, or 112-G will be employed such as any combination of two or more of the electrodes illustrated in FIG. 5. For example, in one such embodiment facial electrodes 112-7 and 112-G may be utilized to detect the facial biopotential signal. By way of further example, in another such embodiment facial electrodes 112-9 and 112-G may be utilized to detect the facial biopotential signal. By way of further example, in another such embodiment facial electrodes 112-9 and neck electrode 112-R may be utilized to detect the facial biopotential signal. By way of further example, in another such embodiment facial electrodes 112-7 and neck electrode 112-R may be utilized to detect the facial biopotential signal. Optionally, the facial electrode 112-G may serve as a grounding electrode. As previously discussed, such electrodes may be contact or non-contact electrodes.

As illustrated in FIG. 5, the facial electrodes 112-1, 112-1, 112-2, 112-3, 112-4, 112-5, 112-6, 112-7, 112-8, 112-9 may be designed or applied for location in particular quadrants of the face as illustrated by imaginary axes shown by axis line SPA and axis line RA. In this regard, the axis line SPA may be considered to be an imaginary axis along a sagittal plane. Axis line RA may be considered an imaginary axis perpendicular to the sagittal axis and running approximately across a vertical middle of a rhinal region of the face. Facial Quadrants QA, QB, QC and QD are considered in relation to axis lines SPA and RA. Thus, facial quadrant QA is considered to be a quadrant that is the sagittal-left and supra-rhinal, which generally corresponds to the upper right side of the face. Facial quadrant QB is considered to be a quadrant that is sagittal-right and supra-rhinal, which generally corresponds to the upper right side of the face. Facial quadrant QC is considered to be a quadrant that is saggital-left and sub-rhinal, which generally corresponds to the lower right side of the face. Facial quadrant QD is considered to be a quadrant that is sagittal-right and sub-rhinal, which generally corresponds to the lower left side of the face.

Accordingly, in some embodiments of the present technology the facial biopotential sensors may be positioned or configured for measurement of particular quadrants of the face. For example, an electrode may be configured as a sagittal-right facial electrode and/or a sagittal-left facial electrode. Similarly, the electrode may also be configured as a sub-rhinal facial electrode and/or a supra-rhinal facial electrode.

In some embodiments of the present technology as discussed in more detail herein, a facial biopotential signal may desirably be measured with one or more sub-rhinal facial electrodes, such as a sub-rhinal, sagittal-right facial electrode or a sub-rhinal, sagittal-left facial electrode. Examples of these may be the facial electrodes shown in FIG. 5 in facial quadrants QC or QD respectively. Optionally, any electrode of quadrants QC or QD may serve as a first electrode and a neck electrode may serve as a second electrode with the voltage difference measured between such first and second electrodes being a facial biopotential signal. Moreover, some embodiments may favorably employ a sub-rhinal, sagittal-left facial electrode as a first electrode, such as any one of the example facial electrodes shown in facial quadrant QC of FIG. 5. In such a case, a neck electrode may serve as a second electrode with the voltage difference measured between the first and second electrodes being a facial biopotential signal. Optionally, the second electrode may be a ground electrode or may be an electrode such as electrode 112-G or an electrode of any of the quadrants QA, QB, QC and QD.

In this regard, it has been discovered that a cardiac vector exists in the head, but unexpectedly it is not an exact spatial translation of the cardiac vector of the chest that is relied on in a typical ECG. The discovered head-based cardiac vector may be considered to be in a saggital plane orientation (front to back), and sensor positioning and configuration in some embodiments of the present technology, such as the orientations discussed in the previous examples, may beneficially be designed to detect facial biopotential signals approximately along this orientation.

In some embodiments of the current technology, the biopotential sensors may simply be applied to a desired location for measurement such as with a temporary adhesive on the patient. However, in some embodiments of the technology, some or all of the head or facial biopotential sensors may be designed or integrated with suitable structures to ensure proper orientation for measurement. For example, in the example case of a respiratory treatment apparatus, the sensors may be embedded, adhered or otherwise integrated with a cushion surface or frame of a patient interface such as a mask (e.g., a nasal mask, nose and mouth mask, or full face mask), nasal prongs or nasal pillows etc., for a respiratory treatment apparatus (e.g., a CPAP apparatus or ventilator apparatus). Similarly, the biopotential sensors may alternatively or in addition thereto, be integrated with a headgear support, such as a strap of a headgear support for the sensors or a strap of a headgear support for a patient interface of a respiratory treatment apparatus (e.g., a nasal mask, nasal prongs or full face mask). Preferably, such integrated sensors may be non-contact or dry contact biopotential sensors. However any of the previously described sensors may be implemented. Examples of the integrated sensor embodiments are illustrated in FIG. 6 through 11.

Figure 6:
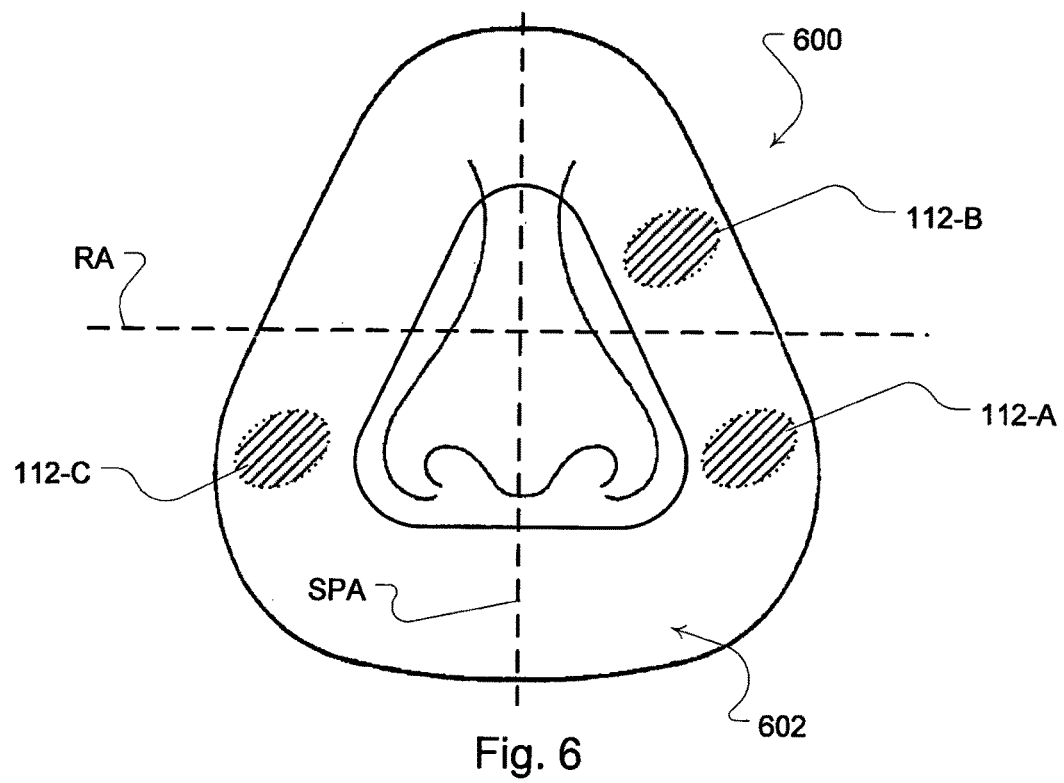
FIG. 6 is an example nasal respiratory treatment mask with integrated biopotential sensors, such as some of the sensors of FIG. 5, of the present technology.

In FIG. 6, a nasal mask 600 includes a cushion 602 that when worn may be compressed to the face around a patient's nose for providing a pressure seal for a respiratory pressure treatment such as a CPAP treatment for sleep disordered breathing. Any of facial electrodes 112-A, 112-B and 112-C may serve as a facial biopotential sensor. Thus, the sensor may be integrated with the cushion 602 or mask frame such that when the cushion is worn, the sensor(s) has a desired orientation for direct or indirect skin contact and may optionally form part of the pressure seal of the mask. In the case of a noncontact sensor, the electrodes may be embedded in the material (e.g., silicone or non-conductive polymer) of the cushion such that a non-conductive material portion of the mask cushion that is part of the pressure seal during use of the mask, lies between the skin of the patient and the embedded electrode. Optionally, the wire leads for the electrodes may be routed within or upon a portion of the patient interface or mask so that the leads may extend to electronically couple with a signal interface of a processor described herein, such as a processor of a respiratory treatment apparatus. For example, these leads may also be integrated with a breathable gas or airflow conduit that extends from the patient interface to direct airflow from a flow generator of a respiratory treatment apparatus. For example in a heated air delivery conduit as described in the Assignees pending U.S. patent application Ser. No. 12/847,021 filed 30 Jul. 2010, the disclosure of which is incorporated herein by reference. Although three electrodes are shown in the example of FIG. 6, i.e., sub-rhinal, sagittal-right facial electrode 112-A, supra-rhinal, sagittal-right facial electrode 112-B and sub-rhinal, sagittal-left facial electrode 112-C, it is understood that one or more may be utilized. For example, in some embodiments of the mask 600 only a single biopotential sensor or electrode may be integrated with the mask cushion 602. In such an embodiment any necessary or desired additional electrode(s) may also be integrated on a headgear support such as described in the examples of FIGS. 8-11 or it may simply be adhered to a skin contact of the patient, such as being temporarily adhered to a neck of the patient.

Figure 7:
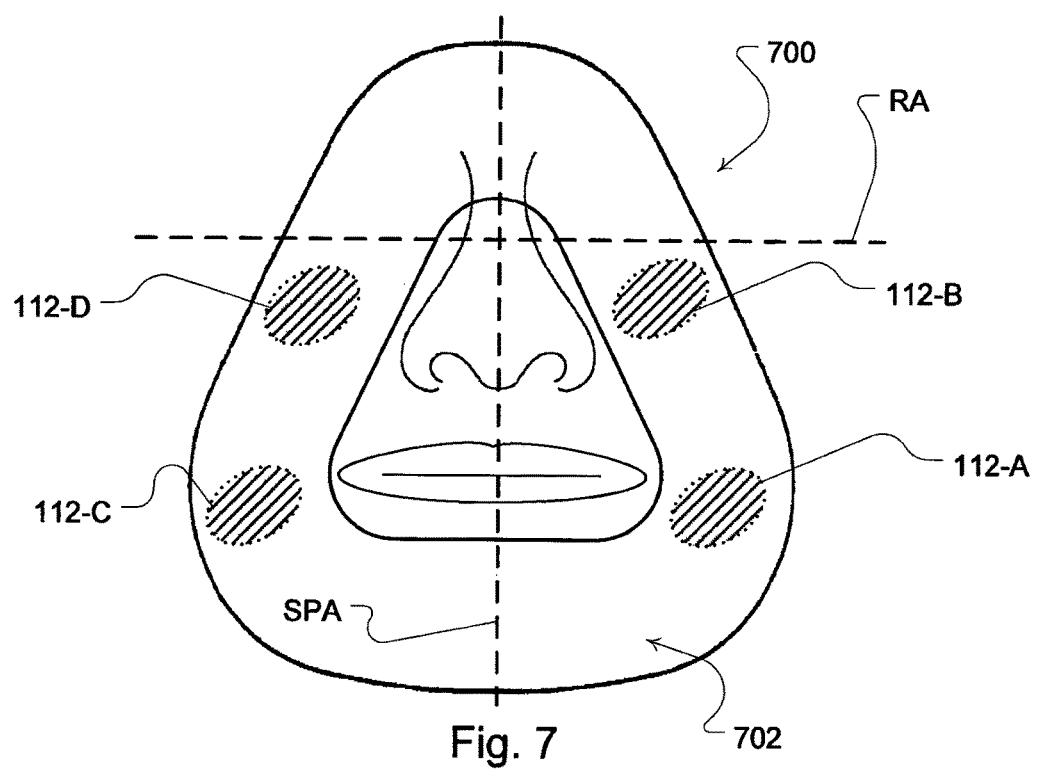
FIG. 7 is an example nose and mouth respiratory treatment mask with integrated biopotential sensors, such as some of the sensors of FIG. 5, of the present technology.

FIG. 7 illustrates a nose and mouth respiratory mask 700 to seal airflow or pressure at the nares and mouth of a patient from respiratory treatment apparatus similar to the mask of FIG. 6. In this example, sub-rhinal facial electrodes 112-A, 112-B, 112-C, 112-D, are integrated with the mask cushion 702 or mask frame. Similar to the embodiment of FIG. 6, this mask may optionally be equipped with any selection of one or more of the illustrated electrodes. In such an embodiment any necessary or desired additional electrode(s) may also be integrated on a headgear support such as described in the examples FIGS. 8-11 or it may simply be in skin contact with the patient, such as being temporarily adhered to a neck of the patient.

FIGS. 8 and 9 depict a mask similar to the mask 700 of FIG. 7. This example embodiment employs one or more facial biopotential sensors integrated with the headgear support 882 for the mask 700, in addition to or alternatively to the sensors of the mask cushion or frame as shown on mask 700. As illustrated, one or more of the sub-rhinal facial electrodes 112-E, 112-F, 112-H and 112-J may be integrated with a mask strap of the headgear support 882 so that the sensors are in contact with or near the surface of the patient's skin when the mask is worn by the patient. In this example, the sensors are integrated at the underside of the straps. Optionally, a neck electrode 112-I may be integrated with the strap for skin contact at or near the neck, such as the back of the neck, strap or neck strap portion 990 of headgear support 882 as shown in FIG. 9.

Figure 10:
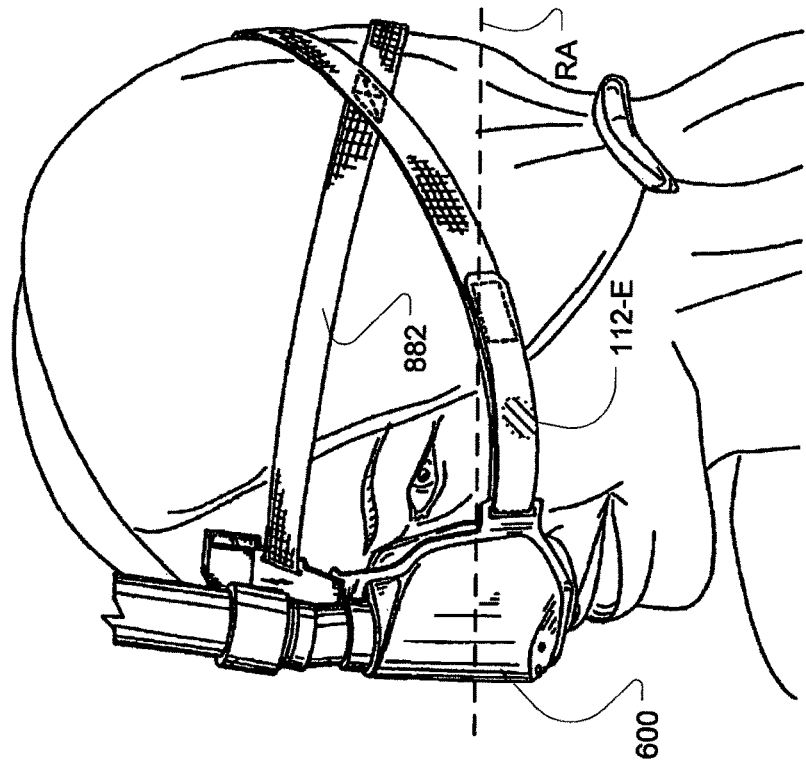
FIG. 10 is a right side view of another respiratory treatment mask with a biopotential sensor integrated in a headgear support for the mask.
Figure 11:
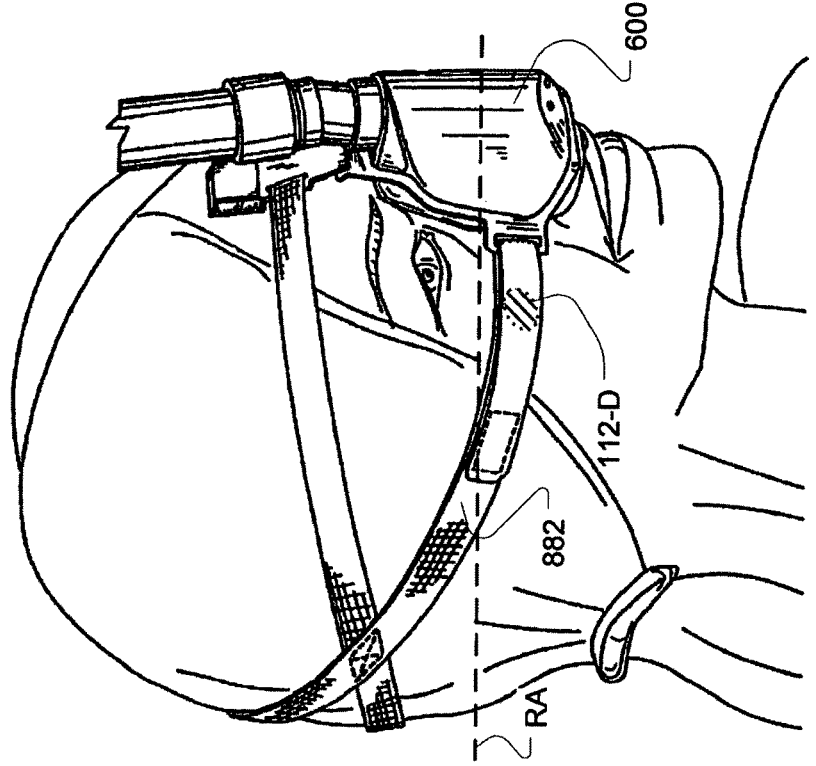
FIG. 11 is a left side view of the respiratory treatment mask of FIG. 10 with an additional biopotential sensor integrated in the headgear support for the mask.

Similarly, FIGS. 10 and 11 depict a mask similar to the mask 600 of FIG. 6. This example embodiment employs one or more facial biopotential sensors integrated with the headgear support 882 for the mask 600, which may be in addition to or alternatively to the sensors of the mask cushion or frame as shown on mask 600. As illustrated, the sub-rhinal facial electrodes 112-E and 112-D may be integrated with a mask strap of the headgear support 882 so that the sensors are in contact with or near the surface of the patient's skin when the mask is worn by the patient. In this example, the sensors are also integrated at the under side of the straps.

Accordingly, an apparatus or device with the cardiac signal detection processor 116 with the facial biopotential sensing technology can provide a convenient way to monitor cardiac related information, such as heart rate or heart rate variability and related conditions, and may even be utilized while a patient sleeps. When such a device determines that a change in the patient's condition is a worsening state, the device can be programmed to provide a warning or message in a form suitable for the patient and/or clinicians to be aware of the status of the patient's heart or condition so that the patient may more efficiently receive the care that is necessary.

The warning or messaging of the system may take a number of forms. For example, the processor or a controller with such a processor, in response to analysis of the cardiac signal, may activate a status light (e.g., an LED or an icon on a display screen or LCD) of the monitoring device. A more detailed message concerning the assessment of the indicator may also be displayed on the display screen. Optionally, the controller may also, or alternatively, send a message to a clinician or physician. Such a message may take the form of a wired or wireless communication. For example, the controller may generate a message via a paging system such as by automatically dialing a paging system. The controller may also be configured to generate an automated voice phone call message. The controller may also send the message by a fax transmission. In some embodiments, the controller may also send a message via any Internet messaging protocol, such as an email message, or by any other internet data file transport protocol. The messages may even be encrypted to keep patient information confidential. A typical message may identify the patient. Such a message may also include the data of the changes recorded by the system and/or any other recorded patient information.

Thus, an example embodiment of a display or warning that may be presented to a patient or physician by the device may be a warning message such as a graphic or textual message advising of a significant change in heart rate or heart rate variability etc. The message may be displayed on the device or a remote device. Optionally, the warning may be an audible alarm.

Example Respiratory Treatment Apparatus

While the technology of the cardiac signal detection processing may be implemented as a stand alone monitoring device, the technology may also be combined with other devices such as a respiratory treatment apparatus as previously mentioned. For example, FIG. 12 illustrates a respiratory treatment apparatus that may implement the sensors and methodologies described herein.

Figure 12:
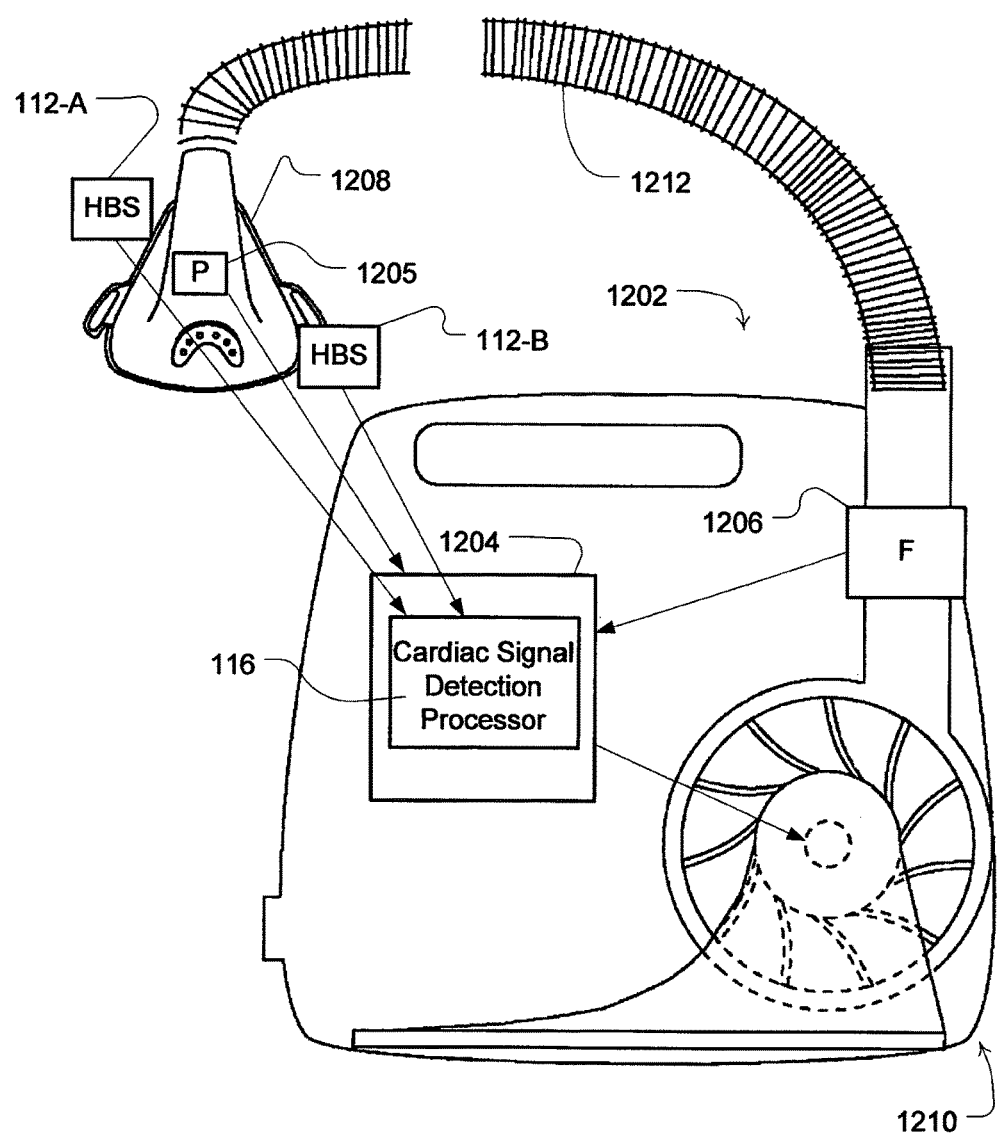
FIG. 12 is an example respiratory treatment apparatus with biopotential sensors and a controller having a cardiac signal detector of the present technology.

In reference to FIG. 12, the respiratory treatment apparatus 1202 may include an attachable patient interface, such as the mask 1208 and gas delivery tube or conduit 1212. In such a device, the delivery tube 1212 may serve as a conduit for leads of the facial or head biopotential sensors (HBS) 112-A and 112-B. The cardiac signal detection processor 116 may then be incorporated with a controller 1204 of the apparatus. The apparatus with the controller may also be configured to provide a respiratory pressure treatment from a flow generator such as a servo-controlled blower 1210. In such a case, the apparatus may optionally include a pressure sensor 1205, such as a pressure transducer to measure the pressure generated by the blower 1210 and generate a pressure signal p(t) indicative of the measurements of pressure. In the illustrated embodiment the pressure sensor 1205 is shown located in the patient interface 1208, however alternatively the pressure sensor 1205 may be located in the device downstream of the blower 1210. In such an arrangement a pressure compensation may made to the pressure measured by the pressure sensor to determine the pressure at the patient interface. The pressure compensation can adjust for the pressure drop along the delivery tube 1212.

The respiratory treatment apparatus 1202 may also optionally include a flow sensor 1206 that may be coupled with the patient respiratory interface. The flow sensor generates a signal representative of the patient's respiratory flow. For example, flow may be measured using a pneumotachograph and differential pressure transducer or similar device such as one employing a bundle of tubes or ducts to derive a flow signal f(t). The flow sensor 1206 may alternatively or additionally be located in the patient interface 1208.

The signals from the sensors (e.g., flow, pressure and biopotential) may then be sent to the controller 1204. Optional analog-to-digital (A/D) converters/samplers (not shown separately) may be utilized in the event that supplied signals from the sensors are not in digital form and the controller is a digital controller.

Based on flow f(t) and pressure p(t) signals, the controller 1204 with one or more processors can generate blower control signals. For example, the controller may generate a desired pressure set point and servo-control the blower to meet the set point by comparing the setpoint with the measured condition of the pressure sensor. Thus, the controller 1204 may make controlled changes to the pressure delivered to the patient interface by the blower 1210. Optionally, such changes to pressure may be implemented by controlling an exhaust with a mechanical release valve (not shown) to increase or decrease the exhaust while maintaining a relatively constant blower speed. With such a controller or processor, the apparatus can be used for many different pressure treatment therapies, such as the pressure treatments for sleep disordered breathing, Cheyne-Stokes Respiration or obstructive sleep apnea (e.g., CPAP, APAP, Bi-Level CPAP, Auto-VPAP, etc.) by adjusting a suitable pressure delivery equation. Optionally, the controller 1204 may also be implemented to make changes to pressure treatment based on detected changes of the metrics derived or detected from the head or facial biopotential signal.

The controller may optionally include a display such as one or more warning lights (e.g., one or more light emitting diodes). The display device may also be implemented as a display screen such as an LCD. Optionally, the display device may be controlled to show data derived from the biopotential signals, such as the determined heart rate or the cardiac signal like the signal graph illustrated in FIG. 4.

In the embodiment illustrated in FIG. 12, the biopotential sensors may generate biopotential signals for the controller or cardiac signal detection processor by communicating the signals in wire leads to the signal interface of the controller or processor. However, in some embodiments, the sensors themselves may be implemented with components for transmitting the biopotential signals to the controller or cardiac signal detection processor by wireless communication. For example, the signals interface of the cardiac signal detection processor or controller may include a receiver or transceiver to communicate wirelessly with one or more transmitters or transceivers integrated with the biopotential sensors HBS. In such a case, data representing the biopotential signal(s) may be transmitted digitally, for example, by any suitable wireless protocol, such as Bluetooth. Optionally, a set of the sensors may share a common transmitter or transceiver for transmission of the data of several sensors to the controller.

Example Controller Architecture

Figure 13:
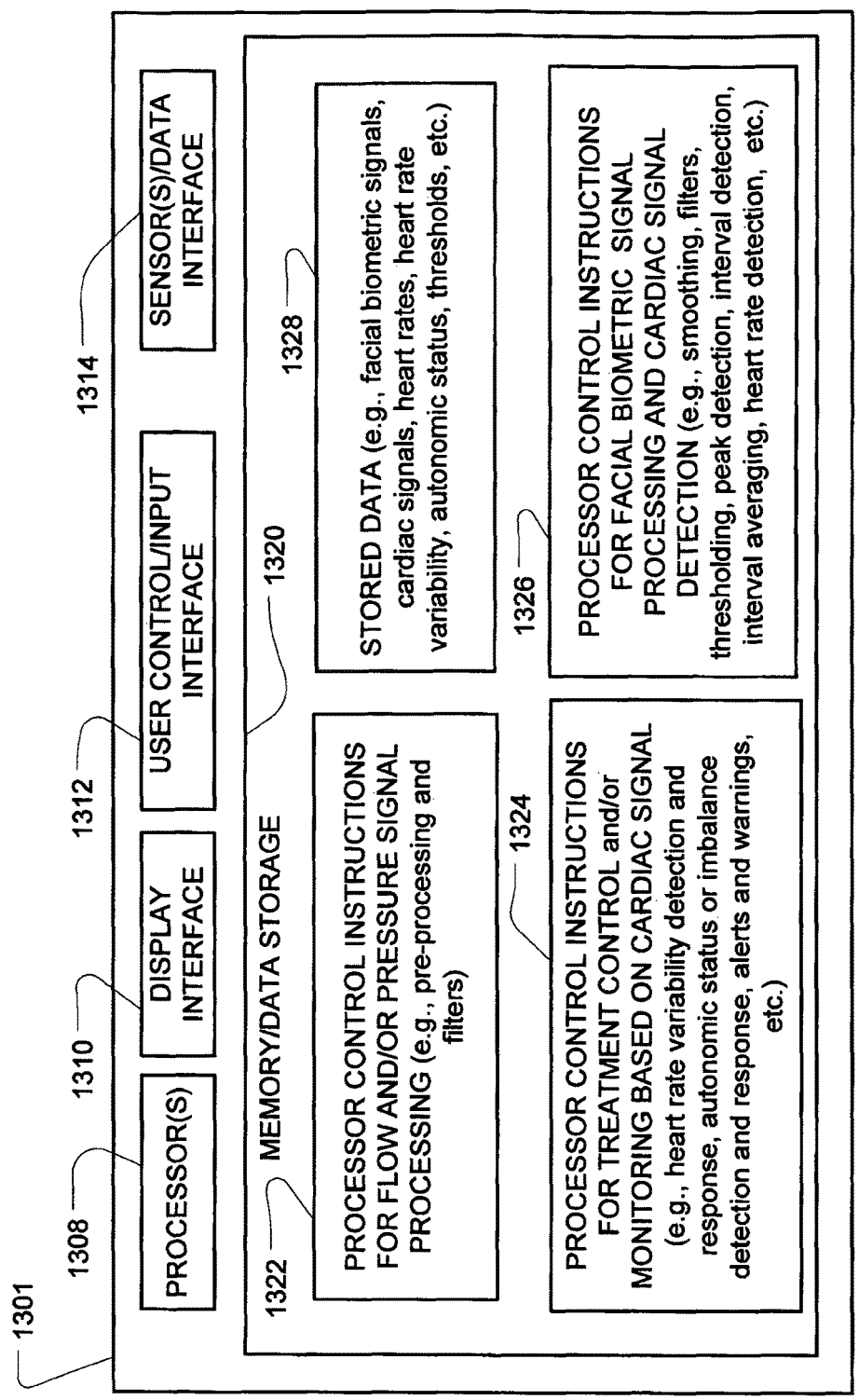
FIG. 13 is an example controller of a cardiac signal detector in some embodiments of the present technology.

An example system architecture of a controller suitable for the present technology is illustrated in the block diagram of FIG. 13. In the illustration, the controller 1301 for the cardiac signal detection processor 116 and/or respiratory treatment apparatus 1202 may include one or more processors 1308. The system may also include a display interface 1310 to output event detection reports (e.g., respiratory rate, heart rate variability etc.), results or graphs (e.g., cardiac signals or biopotential signals as illustrated in FIG. 3 or 4, etc.), as described herein such as on a monitor or LCD panel. A user control/input interface 1312, for example, for a keyboard, touch panel, control buttons, mouse etc. may also be provided to activate or modify the control methodologies described herein. The system may also include a sensor or data interface 1314, such as a bus, for receiving/transmitting data such as programming instructions, pressure and flow signals, facial biopotential signals, cardiac signals etc. The device may also typically include memory/data storage components 1320 containing control instructions of the aforementioned methodologies (e.g., FIG. 2). These may include processor control instructions for flow and/or pressure signal processing (e.g., pre-processing methods, filters) at 1322. These may also include processor control instructions for treatment control and/or monitoring based on cardiac signal detection (e.g., heart rate variability detection and response, autonomic status or imbalance detection and response, alerts and warnings, etc.) at 1324 as discussed in more detail herein. They may also include processor control instructions for facial biometric signal measuring and processing and cardiac signal detection (e.g., smoothing, filtering, thresholding, peak detection, interval detection, interval averaging, heart rate detecting, etc.) at 1326. Finally, they may also include stored data 1328 for these methodologies such as head or facial biometric signals, cardiac signals, cardiac rates, heart rate variability, autonomic status, thresholds, etc.)

In some embodiments, these processor control instructions and data for controlling the above described methodologies may be contained in a computer readable recording medium as software for use by a general purpose computer so that the general purpose computer may serve as a specific purpose computer according to any of the methodologies discussed herein upon loading the software into the general purpose computer.

While the cardiac signal detection technology has been described in several embodiments, it is to be understood that these embodiments are merely illustrative of the technology. Further modifications may be devised within the spirit and scope of this description. For example, while an integrated device is contemplated by the present technology, the methodology of the components of the devices may be shared across multiple components of a system. For example, a monitoring device may simply measure the biopotential signals of the patient and transfer the data representing those signals to another processing system. The second processing system may in turn analyze the data to determine the cardiac signal or related data and metrics therefrom such as the heart rate. The second processing system may then evaluate the generated warning messages as described herein, such as by sending one or more of the described messages, in electronic form for example, back to the patient monitoring device for display on the device to warn the patient. Other variations can be made without departing with the spirit and scope of the technology.

By way of further example, some of the sensors of the present technology may also, or alternatively, be implemented to detect other signals. For example, facial electrodes configured or positioned as previously described herein may also be implemented to detect head, face or skin temperature by equipping one or more electrodes as a facial contact thermistor). Similarly, the electrodes discussed herein may be implemented to detect head, face or skin impedance and/or galvanic skin response (skin conductance). Such signals may then be processed by the aforementioned components to derive further metrics for patient analysis. For example, one or more of the signals previously mentioned may be processed to assess sympathetic activation of the patient.

The invention claimed is:

1. A device to detect a cardiac signal comprising:
   a set of electrodes configured to be positioned for detection of a head-based cardiac vector in a front-to-back orientation in a sagittal plane; and
   a processor, coupled with the set of electrodes, the processor configured to control a detection of a cardiac signal from a head biopotential signal measured with the set of electrodes.

2. The device of claim 1 wherein the set of electrodes comprises a first electrode and a second electrode, wherein the first electrode is a sub-rhinal electrode.

3. The device of claim 2 wherein the first electrode is a sagittal-left electrode.

4. The device of claim 3 wherein the second electrode comprises a grounding electrode.

5. The device of claim 2 wherein the first electrode comprises a portion of headgear.

6. The device of claim 5 wherein the first electrode is formed of a conductive ink.

7. The device of claim 5 wherein the first electrode is a fabric electrode formed of conductive thread.

8. The device of claim 2 wherein the first electrode comprises a portion of a respiratory mask.

9. The device of claim 8 wherein the first electrode is embedded in a non-conductive polymer of a mask cushion.

10. The device of claim 8 wherein the first electrode is a skin contact electrode.

11. The device of claim 8 wherein the first electrode is a non-contact electrode.

12. The device of claim 2 wherein the first electrode comprises a portion of a headgear support for a respiratory mask.

13. The device of claim 1 wherein the set of electrodes comprises a portion of a headgear support for a respiratory mask.

14. The device of claim 1 wherein the processor is further configured to measure the head biopotential signal by controlling a detection of voltage difference between signals of at least two electrodes of the set of electrodes.

15. The device of claim 1 wherein the processor is further configured to measure the head biopotential signal by controlling a determination of field strength with the set of electrodes, the set of electrodes comprising a non-contact sensor.

16. The device of claim 1 wherein the processor is further configured to measure the head biopotential signal by controlling a measurement of current between two electrodes of the set of electrodes.

17. The device of claim 1 wherein the processor is further configured to detect the cardiac signal by processing the biopotential signal.

18. The device of claim 17 wherein the processor is further configured to filter the head biopotential signal.

19. The device of claim 18 wherein the processor is further configured to determine a heart rate from the cardiac signal.

20. The device of claim 19 wherein the processor is further configured to determine the heart rate by detecting peaks within the cardiac signal.

21. The device of claim 20 wherein the processor is further configured to determine the heart rate by determining intervals between detected peaks.

22. The device of claim 21 wherein the processor is further configured to determine the heart rate by filtering the determined intervals to remove determined intervals shorter than a threshold.

23. The device of claim 22 wherein the processor is further configured to determine the heart rate by determining an average of the determined intervals.

24. The device of claim 19 wherein the processor is further configured to determine heart-rate variability based on repeatedly determining the heart rate.

25. The device of claim 1, wherein the set of electrodes comprises more than two electrodes that are positioned for detection of the head-based cardiac vector in a front-to-back orientation in the sagittal plane.

26. A respiratory treatment apparatus comprising:
   a patient interface including a set of electrodes configured to be positioned for detection of a head-based cardiac vector in a front-to-back orientation in a sagittal plane; and
   a flow generator adapted to be coupled to the patient interface, the flow generator to generate a flow of a breathable gas to the patient interface,
   a processor, coupled with the flow generator and adapted to couple with the set of electrodes, the processor configured to control the flow generator, and to control a detection of a cardiac signal from a head biopotential signal measured with the set of electrodes.

27. The apparatus of claim 26 wherein the set of electrodes comprises a first electrode and a second electrode, wherein the first electrode is a sub-rhinal electrode.

28. The apparatus of claim 27 wherein the first electrode is embedded in a non-conductive polymer of a mask cushion.

29. The apparatus of claim 27 wherein the first electrode is a skin contact electrode.

30. The apparatus of claim 27 wherein the first electrode is a non-contact electrode.

31. The apparatus of claim 27 wherein the first electrode is a sagittal-left electrode.

32. The apparatus of claim 27 wherein the second electrode comprises a ground electrode.

33. The apparatus of claim 27 wherein the first electrode comprises a portion of headgear.

34. The apparatus of claim 27 wherein the first electrode is formed of a conductive ink.

35. The apparatus of claim 27 wherein the first electrode is a fabric electrode formed of conductive thread.

36. The apparatus of claim 27 wherein the patient interface comprises a respiratory mask and the first electrode is positioned on a facial contact surface of the respiratory mask.

37. The apparatus of claim 27 wherein the patient interface comprises a headgear support for a respiratory mask, and wherein the first electrode is positioned on a facial contact surface of the headgear support.

38. The apparatus of claim 26 wherein the processor is further configured to determine the head biopotential signal by controlling detecting voltage difference between signals of at least two electrodes of the set of electrodes.

39. The apparatus of claim 26 wherein the processor is further configured to determine the head biopotential signal by controlling a measurement of field strength with the set of electrodes, the set of electrodes comprising a non-contact sensor.

40. The apparatus of claim 26 wherein the processor is further configured to determine the head biopotential signal by controlling a measurement of current between two electrodes of the set of electrodes.

41. A patient interface device for a respiratory treatment apparatus, the patient interface device comprising:
a set of electrodes, including a first facial electrode, the set of electrodes configured to be positioned for detection of a head-based cardiac vector in a front-to-back orientation in a sagittal plane,
the set of electrodes being adapted for coupling with a signal interface of a processor of the respiratory treatment apparatus for detection of a cardiac signal from a head biopotential signal measured with the set of electrodes,
wherein the patient interface device is configured to conduct a flow of breathable gas from a flow generator of the respiratory treatment apparatus.

42. The device of claim 41 wherein the set of electrodes comprises a second electrode, wherein the first facial electrode is a sub-rhinal electrode.

43. The device of claim 42 wherein the first facial electrode is a sagittal-left electrode.

44. The device of claim 43 wherein the second electrode comprises a ground electrode.

45. The device of claim 44 wherein the patient interface device further comprises a respiratory mask and the first facial electrode is positioned on a facial contact surface of the respiratory mask.

46. The device of claim 44 wherein the patient interface device further comprises a headgear support for a respiratory mask, and wherein the first facial electrode is positioned on a facial contact surface of the headgear support.

47. The device claim 44 wherein the first facial electrode comprises a portion of headgear.

48. The device of claim 44 wherein the first facial electrode is formed of a conductive ink.

49. The device of claim 44 wherein the first facial electrode is a fabric electrode formed of conductive thread.

50. The device of claim 44 wherein the first facial electrode is embedded in a non-conductive polymer of a mask cushion.

51. The device of claim 44 wherein the first facial electrode is a skin contact electrode.

52. The device of claim 44 wherein the first facial electrode is a non-contact electrode.

53. A method for detecting a cardiac-related signal comprising:
measuring a head biopotential signal from a set of electrodes connected to a patient and positioned for detection of a head-based cardiac vector in a front-to-back orientation in a sagittal plane; and
detecting by a processor a cardiac signal from the head biopotential signal.

54. The method of claim 53 wherein the measuring comprises determining a voltage difference between signals of at least two electrodes of the set of electrodes.

55. The method of claim 54 wherein the measuring comprises determining field strength with the set of electrodes, the set of electrodes comprising a non-contact sensor.

56. The method of claim 53 wherein the measuring comprises measuring current between two electrodes of the set of electrodes.

57. The method of claim 53 wherein the detecting comprises signal processing of the head biopotential signal.

58. The method of claim 57 wherein the processing comprises filtering the head biopotential signal.

59. The method of claim 53 further comprising determining a heart rate from the cardiac signal.

60. The method of claim 59 wherein the determining the heart rate comprises detecting peaks within the cardiac signal.

61. The method of claim 60 wherein the determining the heart rate further comprises determining intervals between detected peaks.

62. The method of claim 61 wherein the determining the heart rate further comprises filtering the determined intervals to remove determined intervals shorter than a threshold.

63. The method of claim 62 wherein the determining the heart rate further comprises determining an average of the determined intervals.

64. The method of claim 59 further comprising determining heart-rate variability based on repeatedly determining the heart rate.

65. The method of claim 53 wherein the set of electrodes comprises a first electrode and a second electrode, the first electrode being a sub-rhinal facial electrode.

66. The method of claim 65 wherein the first electrode is a sagittal-left facial electrode.

67. The method of claim 66 wherein the second electrode comprises a ground electrode.

68. The method of claim 65 wherein the first electrode comprises a portion of headgear.

69. The method of claim 65 wherein the first electrode is formed of a conductive ink.

70. The method of claim 65 wherein the first electrode is a fabric electrode formed of conductive thread.

71. The method of claim 70 wherein the first electrode is embedded in a non-conductive polymer of a mask cushion.

72. The method of claim 65 wherein the first electrode comprises a portion of a respiratory mask.

73. The method of claim 65 wherein the first electrode is a skin contact electrode.

74. The method of claim 65 wherein the first electrode is a non-contact electrode.

75. The method of claim 65 wherein the first electrode comprises a portion of a headgear support for a respiratory mask.

76. The method of claim 65 wherein the set of electrodes comprises a portion of a headgear support for a respiratory mask.

77. The method of claim 53, wherein the set of electrodes comprises more than two electrodes that are positioned for detection of the head-based cardiac vector in a front-to-back orientation in the sagittal plane.

* * * * *